US009116125B2

(12) United States Patent
Milori et al.

(10) Patent No.: US 9,116,125 B2
(45) Date of Patent: Aug. 25, 2015

(54) METHOD, APPARATUS AND SYSTEM FOR DIAGNOSIS OF STRESS AND DISEASE IN HIGHER PLANTS

(75) Inventors: Debora Marcondes Bastos Pereira Milori, Sao Carlos (BR); Ladislau Martin Neto, Sao Carlos (BR); Ednaldo Jose Ferreira, Sao Carlos (BR); Ana Flavia Zaghi, Sao Carlos (BR); Andre Leonardo Venancio, Sao Carlos (BR)

(73) Assignee: EMPRESA BRASILEIRA DE PESQUISA AGROPECUARIA—EMBRAPA, Brasilia (BR)

( * ) Notice: Subject to any disclaimer, the term of this patent is extended or adjusted under 35 U.S.C. 154(b) by 876 days.

(21) Appl. No.: 13/139,969

(22) PCT Filed: Oct. 14, 2009

(86) PCT No.: PCT/BR2009/000317
§ 371 (c)(1),
(2), (4) Date: Feb. 1, 2012

(87) PCT Pub. No.: WO2010/069017
PCT Pub. Date: Jun. 24, 2010

(65) Prior Publication Data
US 2012/0123681 A1    May 17, 2012

(30) Foreign Application Priority Data

Dec. 15, 2008 (BR) ..................................... 0805608

(51) Int. Cl.
*G01N 21/64* (2006.01)
(52) U.S. Cl.
CPC ...... *G01N 21/6486* (2013.01); *G01N 2201/129* (2013.01)

(58) Field of Classification Search
CPC .................................................. G01N 21/6486
USPC ............................................................ 702/2
See application file for complete search history.

(56) References Cited

U.S. PATENT DOCUMENTS

| 7,597,936 B2 * | 10/2009 | Smith et al. ................. 427/419.1 |
| 2004/0021860 A1 | 2/2004 | Gardner, Jr. et al. |
| 2004/0108452 A1 * | 6/2004 | Graber et al. .................. 250/281 |

FOREIGN PATENT DOCUMENTS

| CN | 1824802 A | 8/2006 |
| CN | 101074926 A | 11/2007 |
| JP | 2004-264101 A | 9/2004 |
| JP | 2006-267092 A | 10/2006 |
| WO | 2007/021485 A2 | 2/2007 |

* cited by examiner

*Primary Examiner* — Bryan Bui
(74) *Attorney, Agent, or Firm* — Sughrue Mion, PLLC

(57) ABSTRACT

The present invention relates to a method, apparatus and a system of fast diagnosis of stresses and diseases in higher plants. The proposed methodology is based on the hypothesis of that when a plant is in imbalance; there are changes in its metabolism that render an alteration of the chemical composition of its organs. This chemical alteration leads to a change in the physical properties, such as the fluorescence of the leaves. Due to the complexity of the material of the leaves, the present method proposes that the signal be treated with statistical methods and that the classification is made through softwares based on machine learning. As an example of the application of the invention, the results are shown for the Greening disease in citrus. Currently, Greening is the most severe citrus disease since there is no treatment available for it and due to its high dissemination rate and the fact that it affects all varieties of orange trees, being the diagnosis performed through visual inspection, which renders high subjectivity, high error percentage and the disease is only diagnosed after the expression of the symptoms (~8 months). During the asymptomatic phase, the infected tree is a source of dissemination of the disease. The present invention can perform the asymptomatic diagnosis of Greening disease from the leaf with a percentage of correct diagnosis higher than 80%.

25 Claims, 7 Drawing Sheets

METHOD, APPARATUS AND SYSTEM FOR DIAGNOSIS OF STRESS AND DISEASE IN HIGHER PLANTS

CROSS REFERENCE TO RELATED APPLICATIONS

This application is a National Stage of International Application No. PCT/BR2009/000317, filed Oct. 14, 2009, claiming priority based on Brazilian Patent Application No. PI 0805608-0, filed Dec. 15, 2008, the contents of all of which are incorporated herein by reference in their entirety.

FIELD OF THE INVENTION

The present invention relates to a method, apparatus and system for the fast diagnosis of stresses and diseases in higher plants. It will be presented as an example the case of the Greening disease in citrus in which the diagnosis is performed from the leaf using the said apparatus based on fluorescence spectrometry containing software for the treatment and classification of the data.

BACKGROUND OF THE INVENTION

Brazil, since the beginning of the '90s, stays as the major world producer of orange, being responsible for 80% of the international trade of concentrated and frozen orange juice. In order to obtain this production, estimated in US$900 million, about US$410 million of input is spent, leading to approximately US$1.5 billion in transactions involving the marketing of citrus products, such as juices and fresh fruit (FNP Consultoria & Comércio, 2008. Available at <http://www.fnp.com.br/agricultura/citros/prod_area_laranja.php> Access in Sep. 23, 2008). The second major producer is the United States, followed by Mexico, China and Spain. Spain and the United States are the main exporters of fresh fruit, which corresponds, respectively, to 38 and 18% of the world exports (BOTEON, M.; VIDAL, A. J. Citricultura no Brasil e na Flórida. Citricultura Atual, n. 23, p. 3, 2001).

The state of São Paulo (Brazil) has around 34.2 million of plants under development and 163.5 million citric plants in production, reflecting more than 80% of the national production of citric fruits. Currently, it is responsible for 97% of the Brazilian exports, being the grand dynamic core of the Brazilian citrus complex. This market is responsible for approximately US$1.5 billion of currency for the country, state and cities and employs 400 thousand people. The citrus park of São Paulo together with a region in Minas Gerais known as "Triângulo Mineiro" presents 198 million trees. The harvest of oranges is performed throughout the year due to the composition of the varieties such as "Hamlin", "Lima", "Pêra", "Seleta", "Bahia", "Natal", "Valência" and "Folha Murcha". Among these, some are appropriate for the production of juice, such as "Pêra", which represents 38% of the total of the trees, followed by "Valência", "Natal" and "Hamlin", with respectively 17, 25 and 7% (BARROS, M. H. C.; BOTEON, M. O Brasil é o único país paie produz o ano inteiro. Hortifruti Brasil, v. 3, p. 21, 2002.).

With the advance of the technology in the field, the plants started to be multiplied by grafting, which rendered great advantages regarding the precocity and uniformity of the orchards. However, at the same time it reduced the variability, making the culture a constant target to several pests and diseases which, when facing favorable conditions to their development, are capable of causing irreversible damage. The phytosanitary costs, along with the fertilizers, are higher than 60% of the cost of production. The quality and the quantity of the citric fruits are frequently threatened due to the damage left in the plants, which, depending on the intensity of the attack, can make it unproductive or lead to its eradication.

In the middle of 2004 a new disease was reported in the orchards from São Paulo. A devastating disease without cure originated from Asia and Africa. Huanglongbing (HLB), also known as Greening, is currently the most feared disease among the orange producers due to the fact that it does not possess cure or treatment, since it has a high rate of dissemination and affects all the commercial varieties of oranges. The most efficient solution until this moment in order to minimize the losses is the eradication of the plants as soon as a positive diagnosis for the disease is confirmed.

The Greening disease has as causing agent a bacterium that lives in the phloem of the host plant, being known as *Candidatus* Liberibacter. There are three types of bacteria related to Greening, *Candidatus* Liberibacter africanus, *Candidatus* Liberibacter asiaticus and *Candidatus* Liberibacter americanus, being the latter the main causing agent in the state of São Paulo. The symptoms of Greening are visually the same, disregarding where the disease occurs. Initially, the symptoms appear in the branches, which are evident due to the yellow coloration contrasting with the green coloration of the leaves from the non affected branches. The leaves present pale yellow coloration, with green sectors, rendering irregular and asymmetric spots (mottled). The fruit becomes deformed and asymmetric. The white part of the peel, in some cases, presents thickness higher than normal. The reduction in the size of the fruit and intense fall also occur.

Due to the lack of a cure, the Greening disease is, currently, the most feared diseases in the culture of citrus. It was already responsible for the eradication of more than 2 million citrus trees and the great majority of them were in the season of higher productivity.

In particular, the culture of citrus of the state of São Paulo presents some peculiar characteristics that lead to a high vulnerability of the culture to the occurrence of epidemics of known diseases such as Decline disease, and of new diseases, such as the Citrus Sudden Death (CSD) and Greening disease, rendering important consequences to the sustainability of the agribusiness:

1) The orchards of citrus of the state of São Paulo occupy a nearly continuous area of approximately 615,300 ha (FNP. Citrus. AGRIANUAL 2003: anuário da agricultura brasileira. FNP consultoria & agroinformativos, São Paulo, p. 295-314, 2003.), without great variations of relief or physical barriers and with high traffic of people between them;
2) The citric plants are perennial and, therefore, are exposed throughout the year and for several years to the attack of pests and diseases. Besides that, the emission of new shoots can be observed during a great part of the year, which confers a continuity of susceptible tissue and of inocule between the cultivation seasons;
3) The orchards of the state of São Paulo present a very low genetic variability. Only four varieties of sweet orange (*Citrus sinensis* Osbeck): 'Pêra-Rio', 'Natal', 'Valencia' and 'Hamlin', propagated vegetatively through grafting, represent 92% of the Brazilian citrus culture. The rootstock used in approximately 85% of the trees is the 'Cravo' lime (*C. limonia* Osbeck) due to its rusticity, vigor conferred to the canopy and resistance to the hydric deficiency of the north and northwest of the state.

Currently, there are some diagnosis methods for Greening disease. The most common diagnosis is performed through the visual inspection of leaves presenting the symptoms of the disease. The control of the Greening disease in the state of São Paulo and in the "Triângulo Mineiro" has been achieved through periodic visual inspections performed by technicians of the Fundecitrus or people trained by them. This method has as its characteristics a high rate of subjectivity and a high percentage of error, besides the fact that the disease is only diagnosed after the expression of the symptoms, which is, after a long period of asymptomatic phase of the tree (approximately 8 months). During the asymptomatic phase of the disease, the infected tree is an invisible source of dissemination of the disease leading to a very large delay in the eradication of the tree. However, after the visualization of the symptoms, the uprooting is the only current matter of control of the disease.

The document JP2006267092-A described a detection kit for Greening disease in early stages, based on the recognition of the drop in the manganese and iron concentrations in the tissues of the infected tree. The detection procedure includes the obtaining of a water soluble extract of plant material containing a buffer system, followed by analysis of absorption spectrophotometry. The disease determination, however, is unspecific, since the low manganese and iron concentrations in a plant can be due to several physiological causes, including deficiency of these minerals in the plant nutrition. In an analogous manner, the document JP2004264101-A claims the detection of the Greening disease in plant extracts via the analysis of the starch concentration through the iodine reaction, thus presenting, the same disadvantage in the physiological unspecificity of the deficiency.

A method described in the document WO2007021485-A2 promises the detection of Greening causing bacteria, among the detection of several other pathogens and chemical contaminants from plants and animals, using the Raman Effect of applied polarized radiation scattering. However, the detection is conditioned to aqueous samples that are submitted to a complex treatment that includes drying over colloidal metallic surface, followed by contact with ultra filtering membrane.

The Apta Citrus, affiliated to the Instituto Agronômico de Campinas (IAC), is the only center of the state of São Paulo to provide technical reports for the diagnosis of Greening disease. This report is based in a technique called PCR (Polymerase Chain Reaction), which consists in the genetic analysis of the leaves in search for the DNA of the Greening causing bacteria. However, the detection of the bacteria DNA is only possible in symptomatic leaves (mottled), and even then, it can fail in 10% of the cases. For the diagnosis in asymptomatic leaves (without visible signs of the disease), the IAC uses a more complex variation of the technique called real time PCR, which its sensitivity is at least 1000 times higher than the conventional technique. However, in function of its complexity, the real time PCR has not been used in routine exams, only for scientific work. Even though the PCR technique is highly efficient, it is costly and laborious (BOVÉ, J. M. History, etiology, field identification, transmission, and world distribution of huanglongbing: a destructive, newly-emerging, century-old disease of citrus. Huanglongbing Greening International Workshop, v. 1, p. 1, 2006) The cost of the analysis per sample, using the conventional PCR, is around US$25.00 and a report can take around 20 days. The use of PCR in large scale is economically unviable; besides the fact that it produces an infestation mapping that is very temporally delayed. On the other hand, the document CN1824802-A claims the detection of the asymptomatic trees in only 3 h after the sampling, but it is restricted to the detection caused by the bacteria Candidatus Liberobacter asiaticum Jagoueix and to the citrus of the mandarin type.

It is in this moment that the fluorescence becomes a relatively simple and efficient dispositive that can make a difference. The fluorescence is a technique that allows the detection of chemical alterations that occurs in the leaves of plant affected by Greening and by other diseases prior the perception of their visual manifestations.

In the document BR200201249-A, the auto-fluorescence of the leaves, fruits and branches allows the detection of the citric canker in asymptomatic citrus, after the exposition to light sources with short wavelength. However, the technique is limited to the detection of this disease, caused by the bacteria *Xanthomonas axonopodis* pv. *citri*.

This invention developed in the Embrapa Instrumentação Agropecuária has as its objective to protect a new diagnosis methodology and apparatus for diagnosing stresses and diseases in higher plants, such as the citrus Greening disease. A work previously performed in the Laboratório de Óptica e Lasers da Embrapa Instrumentação Agropecuária LOLEIA (document PI 05059757-7), demonstrated the possibility of distinction of healthy leaves from sick ones, and also, of distinction of diseases (CSD and Decline) through the ratio of the maximum of the fluorescence emission spectrum using commercial spectrometers. The basic idea of the proposed methodology was the following: when a plant reaches imbalance, being caused by stress or by disease, changes in its metabolism occur that lead to an alteration of the chemical composition of its organs. This chemical change leads to a change in the physical properties, such as, for example, reflectance and fluorescence of the leaves. Based in this hypothesis, it was developed a laboratory study using commercial apparatus, regarding the fluorescence emission of the leaves of healthy and sick citrus leaves. The possibility of distinction of healthy trees, tress with Decline or CSD was observed through the ratio of fluorescence emission peaks, method described in PI 05059757-7.

In the patent application PI 05059757-7, the idea of a portable module that performs spectroscopic measurements in leaves was protected for the diagnosis of citrus sudden death with excitation using bulb, led or laser in the range of 420 to 480 nm. In 2006, the LOLEIA developed a system using laser induced fluorescence spectroscopy (LIFS), similar to the one proposed in the document PI 05059757-7, with a probe constructed with optical fibers and detection system constituted of a set of calibrated photodiodes that permits the obtaining of the emission spectrum of the leaf in an extremely quick manner (~1 s) and excitation with laser at 470 nm. With this new system, it became possible to analyze a large volume of samples in reduced time. At that time, Greening disease was already considered the most severe disease of the Brazilian citrus sector, and, therefore, the LOLEIA initiated research in order to evaluate the possibility of diagnosis of Greening using fluorescence spectroscopy. With the preliminary results, it could be observed that the best distinction for the Greening disease was observed with other laser with 561 nm wavelength excitation. With the reformulated portable module, a discerning study to evaluate the possibility of the diagnosis of Greening through the leaves was performed. From this study, a new disease diagnosis methodology different from the one of the patent application PI 05059757-7 (for CSD) was resulted. Even though the current methodology uses similar apparatus protected for the CSD, with different excitation wavelength, the system as a whole is totally different and main differences will be discussed below.

In the current system, the ratios of peaks are not used as in the document PI 05059757-7. It was developed a software to collect the fluorescence spectra and to perform an statistical treatment of them (FIGS. 1 and 2) in order to evaluate in the most discerning manner all the emission spectrum to obtain a higher number of information that enables a more precise diagnosis of the diseases.

After being treated by the Principal Component Analysis (PCA) statistical method, agglomerations in tridimensional graphics of the first main components were clearly defined as shown in FIG. 3.

As the system became very sensitive, it also distinguished the variety of the canopy and of the rootstock, reason why another patent application was elaborated with this theme, the "Método e Equipamento para Certificação de Mudas de Citros" (Method and Equipment for Certification of Citrus Seedlings). This way, for each combination of canopy and rootstock, a system calibration process was performed. For each combination of canopy and rootstock, a set of samples containing healthy and sick leaves were used in order to provide information to the system of typical spectra of each class of samples. In general, the following classes were evaluated: healthy samples, sick samples presenting Greening in the symptomatic phase, sick samples presenting Greening in the asymptomatic phase, with CSD and with Decline.

Using tools of machine learning, another software was developed in such way that the calibration database was used in a manner that the system could be capable of measuring a totally unknown leaf and classifying the tree status as healthy or sick, and, if sick, identifying the disease. In the case of Greening disease, it was possible to identify the disease in the symptomatic phase as well as in the asymptomatic phase. This result shows the great potential of the technique for enabling the performance of early diagnosis of the disease.

In the patent of CSD, the spectroscopy analysis was only performed after the obtaining of a map of the orchard through fluorescence images, which performed a distinction of healthy trees from sick ones. In the current patent, the diagnosis is performed using only the fluorescence spectroscopy.

Therefore, different from the patent PI 05059757-7, the apparatus as it was protected per se is not capable of performing an automatic diagnosis. The complete system needs the acquisition software and statistical treatment of the data, calibration database and classifying software. This way, in this patent, the protection of the complete system composed by the apparatus for performance of fluorescence spectroscopy measurements, the acquisition software and statistical treatment of the data, database and classifying software for the performance of the diagnosis of Greening through the citrus leaves is requested.

SUMMARY OF THE INVENTION

The present invention shows that stresses and diseases in higher plants, such as Greening, for example, the main current problem of the Brazilian culture of citrus, can be detected in a quick, precise, early and economically viable manner by the means of fluorescence spectroscopy performed directly in the leaves and other parts of the plant, together with the creation of a database and prediction models or statistical, mathematical and/or computational discrimination of machine learning, contributing, this way, for the control of diseases.

The first embodiment of the present invention is a Method for the diagnosis of diseases and stresses in higher plants, particularly Greening, wherein the following steps are comprised:

a) Calibrating the classifying software, collecting the emission spectrum of at least 150 leaves from the sick trees and 150 leaves from healthy trees;

b) Collecting at least 03 leaves from each georeferenced tree of the orchard to be analyzed;

c) Detecting and measuring the fluorescence emission spectrum of all the leaves collected in (b);

d) Analyzing the spectra generated in (c); and e) Generating a report for each tree.

f) Based on the coordinates and in the report for each tree, construction of a health status map of the orchard.

A second embodiment of the present invention is an apparatus for the diagnosis of diseases in higher plants wherein it comprises an excitation source, an excitation optical cable, an adjustable optical filter, an optical fiber adaptor, a mixed optical cable, a probe, an emission optical cable, a mini spectrometer and a data processing classifying software.

An additional embodiment of the invention is a system wherein the said method is used for the diagnosis of diseases and stresses in higher plants in association with an apparatus of spectroscopy for the diagnosis of diseases and stresses in higher plants, through the fluorescence emission spectroscopy.

DETAILED DESCRIPTION OF THE INVENTION

At first, in order to develop the method proposed in this invention, a spectroscopic characterization of the leaves and photosynthetic pigments extracted from the leaves was performed in order to observe the spectral differences between a healthy material and a sick one, using a conventional fluorescence spectrometer.

After this study, alterations in an apparatus developed for the diagnosis of CSD (PI 05059757-7) were performed in order to make possible the diagnosis of Greening. However, modifications restricted to optical alterations in the apparatus were not sufficient.

Figure 5:
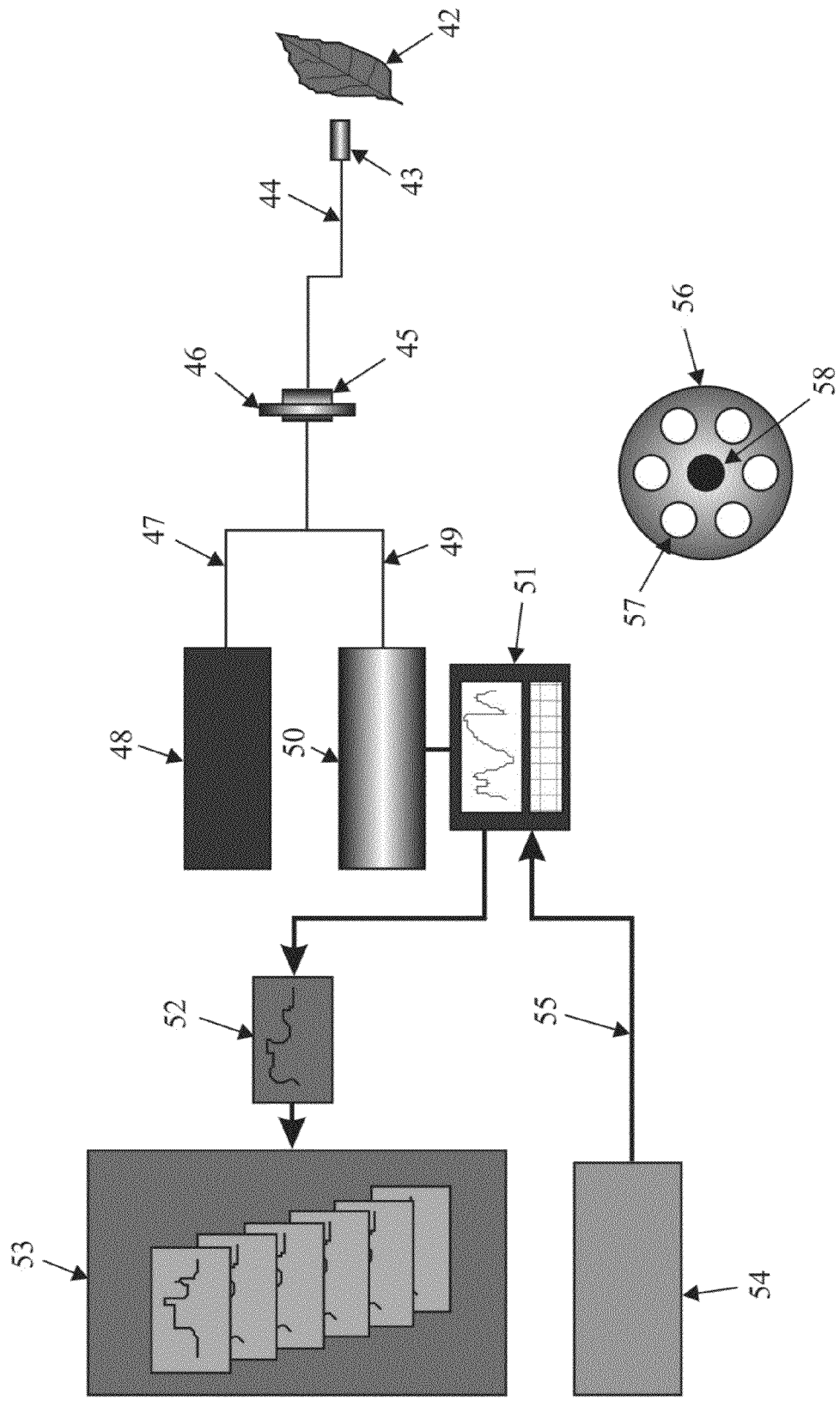
FIG. 5—Apparatus for the diagnosis of the Greening disease.

In FIG. 5, a schematic representation of the developed new system, object of the present invention, is shown. 42—citrus leaf to be analyzed; 43—probe; 44—optical cable; 45—optical fiber adaptor; 46—regulatable filter; 47—excitation optical fibers; 48—diode laser; 49—emission optical fiber; 50—mini spectrometer; 51—laptop; 52—signal/data treatment; 53—database; 54—classifying software; 55—report; in the inset the lateral profile of the probe is shown (56), that contains the following parts: 57—excitation optical fibers; and 58—emission optical fiber.

A new methodology for the diagnosis of Greening was developed which is also object of the present invention. The methodology is composed of three steps:

1—Construction of a database—Initially, the system requires a database with information of possible fluorescence emission spectra of a leaf from a given combination of canopy and rootstock. In order to achieve that, at least 150 leaves from healthy trees, 150 leaves of symptomatic sick trees and 150 leaves of asymptomatic sick trees are collected. The spectra of these 450 leaves are captured by the apparatus of the present application, which patent is being requested, and are treated by statistical methods through a software also developed especially for this apparatus.

Figure 1:
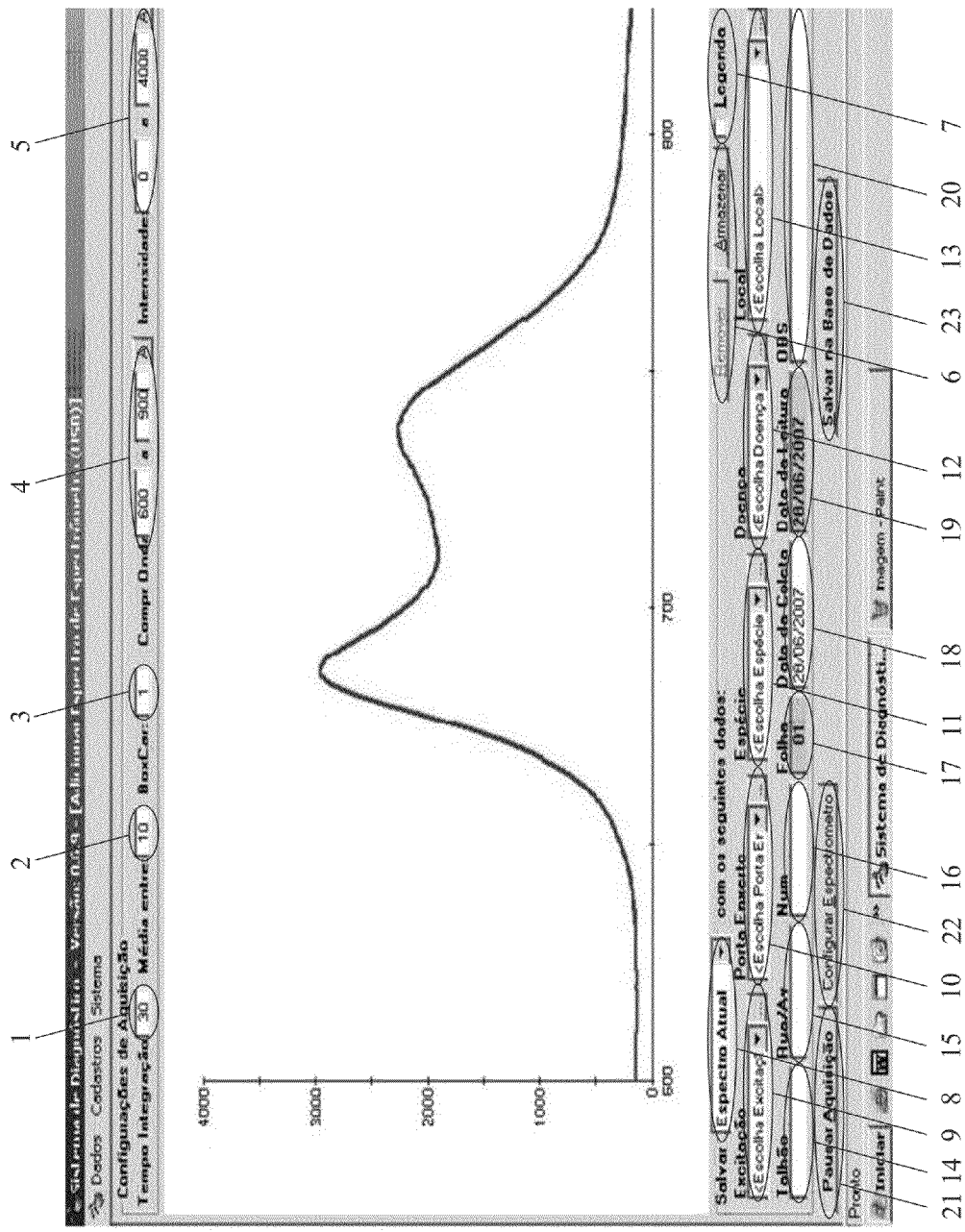
FIG. 1—PrintScreen of the acquisition software.

The program developed for the collection of the data allows the adjustment of several acquisition parameters (FIG. 1), among which is the integration time (in ms), that is the time interval in which the mini spectrometer harvests light before sending to the program the information about the spectrum (1). It also allows modifying the number of collections that the program performs in order to compose, through average calculation, a single spectrum (2); which is a useful procedure in the noise reduction. There still is the boxcar adjustment (3), which controls the intensity of the smoothening of the spectrum applied by the program.

Another class of adjustable elements in the main screen is regarding the visualization of the collected spectra. It is possible to determine the lower and higher wavelength limits exhibited on the screen, in nm (4), as well as the intensity limits (5), in arbitrary units. It is still possible to visualize one or more collected spectra, as well as remove them from the screen later (6). In this case, the spectra are exhibited in different colors, and the user has the option of accepting or disabling an automatically generated subtitle (7).

In the event of the presence of more than one spectrum in the screen, it is necessary that the user specifies which of them must be saved in the database (8). In order to save a spectrum, however, it is necessary to provide the description of it, such as the excitation nature that generates it (9) and of the analyzed sample. The mandatory data about the sample are: the rootstock varieties (10) and the canopy varieties (11), the disease that is infecting the plant (12) and the local of origin of it (13). The set of options for each one of the cases can be edited by clicking the right button of the respective fields.

There are still data about the sample that must be filled by the user himself: the number of the plot (14), of the street (15), of the number (16), which identify the plant and the date of the collection of the sample (18). The number of the leaf (17) is automatically attributed by the program, in order to avoid confusion in the event of existence of more than one sample proceeding from the same plant. The date of spectrum acquisition (19) is also automatically registered. The program still allows the registration of additional observations which the user may need to do about the sample in question (20).

Through the acquisition screen the user can also start or interrupt the instantaneous visualization of the data in the screen (21), access the configuration of the mini spectrometer (22) and, finally, save in the database the spectrum currently selected, together with the inserted information in the respective fields (23).

Figure 2:
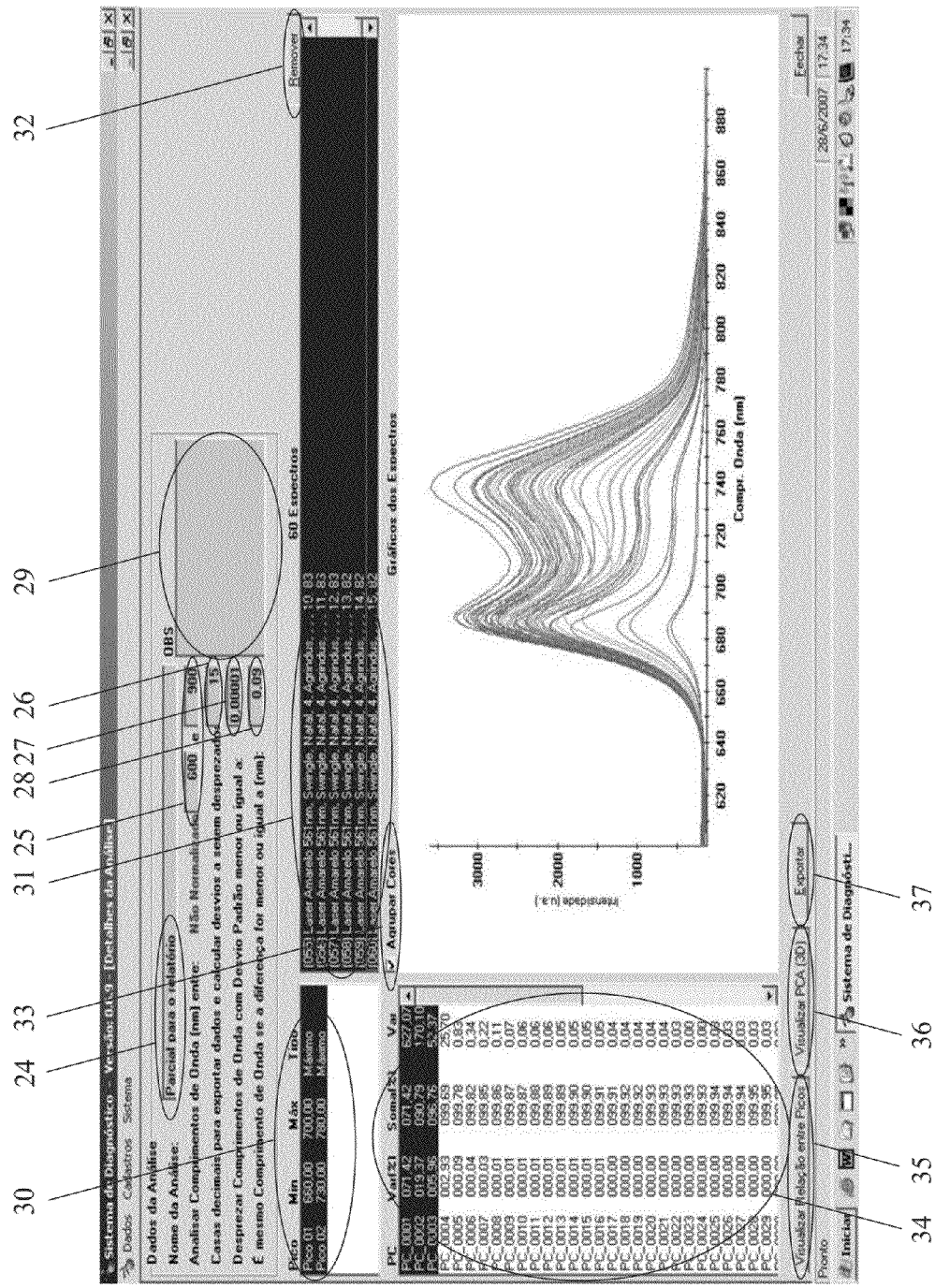
FIG. 2—PrintScreen of the software for the data treatment.

The analysis of the stored data (FIG. 2) must be identified by a name chosen by the user (24). This must also select the spectra range to be used in the analysis (25) and specify the number of decimal separators to be taken into consideration (26). There is still the option of choosing the limit value of the standard deviation associated to each wavelength, variables which the standard deviation is lower than this limit are disregarded, in order to avoid the occurrence of division by zero (27). Another problem is avoided through the establishment of a minimum difference between two wavelengths as requisite for the consideration by the program as distinct variables (28). This prevents that any occasional minimal difference of round off of the wavelength value performed by the program results in error in the analysis. There is also an available field (29) for the user to register the observations about the analysis in question.

It is possible to select the spectra that are visualized in the screen (31), to choose to distinguish them or not, through the employment of different colors (33), to exclude from the analysis the selected spectra (32) or export them in a format that is compatible with other programs (37).

The available analysis proceedings are the calculation of the quotient between the intensities of the maximum and minimum points and the PCA. In the first case, the user can choose the limits of the two intervals, in which the maximum (or minimum) point that will be used for the index determination (30) will be calculated, and can also graphically visualize the result (35). In the second case, the user must choose three main components (34) in order to visualize the three dimensional graph which contains them (37).

Figure 3:
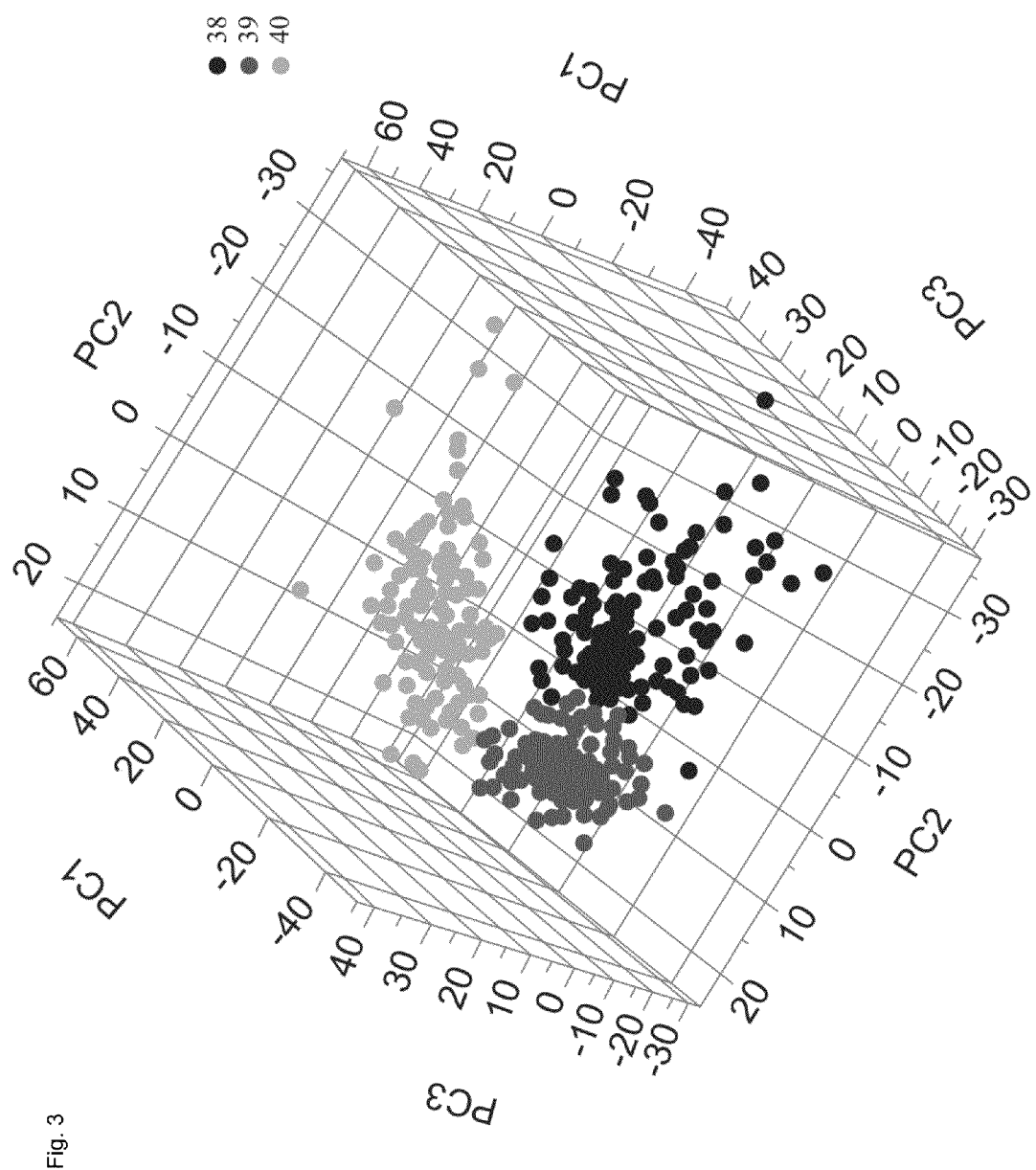
FIG. 3—Graph of the three first main components generated from the emission spectra of fluorescence captured by the portable system developed by LOLEIA for trees of sweet orange ("Pêra") in healthy Sunky rootstock (38), with symptomatic Greening (39) and asymptomatic for Greening (40).

This way, a three dimensional graph is obtained (FIG. 3) with agglomerations that separate the different classes of trees (healthy (38), symptomatic (40) and asymptomatic (39)) and a database with characteristic information of each sample class.

2—Classifying software—Using tools of machine learning, statistics and/or mathematics and the database, a classifying model is developed.

Figure 4:
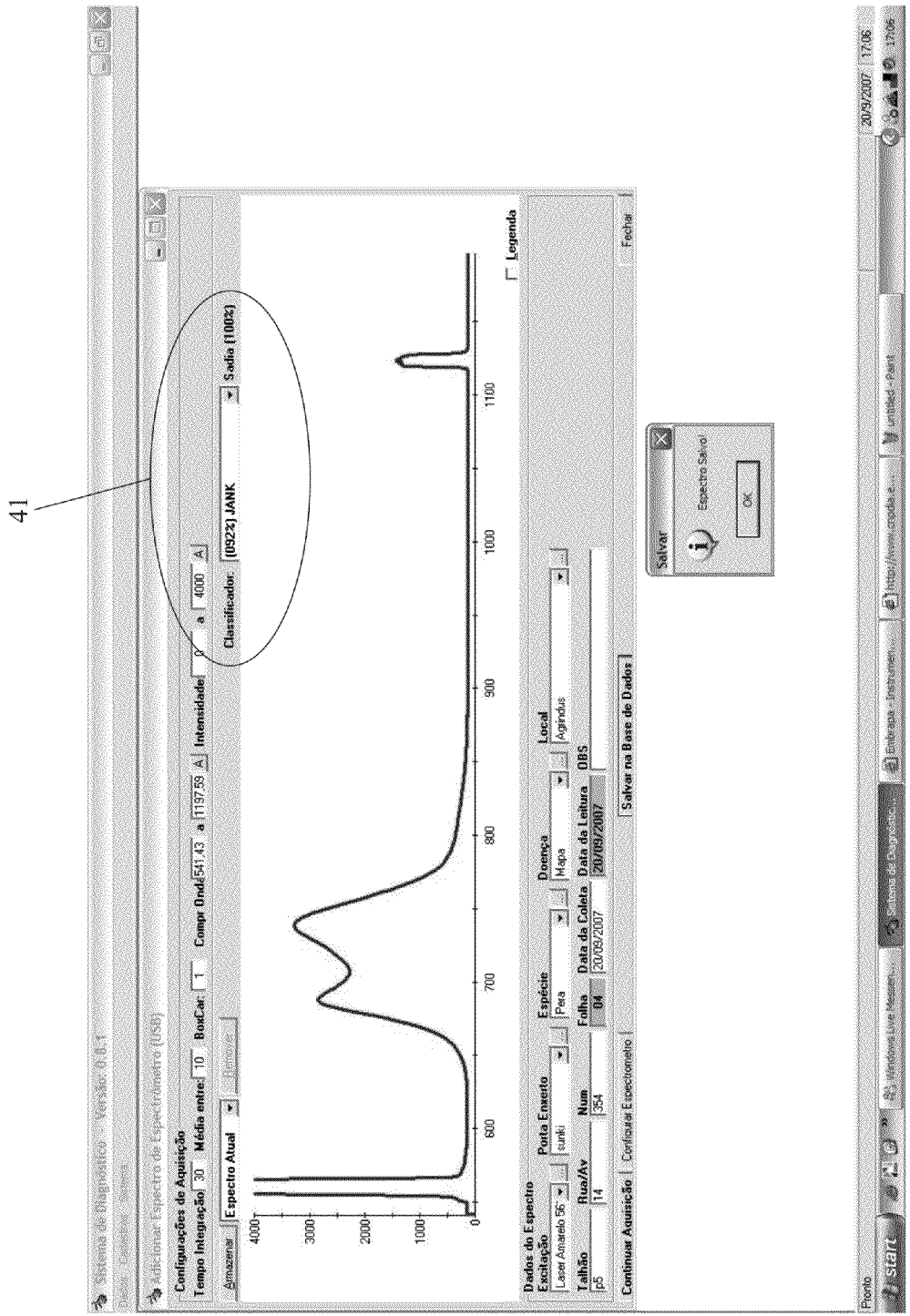
FIG. 4—PrintScreen of the classifying software highlighting the classification window (41).

In FIG. 4, the window where the leaf diagnosis is shown is indicated (41). The classification is practically instantaneous for the spectrum which was just saved and the diagnosis provided according the criteria of a classifier previously generated. Together with the result, the screen exhibits an estimative of the confidence degree of performed diagnosis (41). The user has the option of changing, at any moment, the classifier in use for another that is available in the database of the program.

3—Orchard evaluation—At least 3 leaves of each tree of the orchard is collected. The trees are georeferenced in order to render the construction of the infestation map. The emission spectrum of the leaves is measured and the report for each tree is obtained by the prevalence of resulting diagnosis of the collected leaves. This way, each georeferenced tree has a report and it is possible to construct an infestation map.

In experiments performed with the new apparatus and methodology in a plot of 1000 of trees of "Pêra" orange in "Cravo" lime rootstocks an index of correct results higher than 80% was obtained, even in asymptomatic trees.

EXAMPLE

Figure 6:
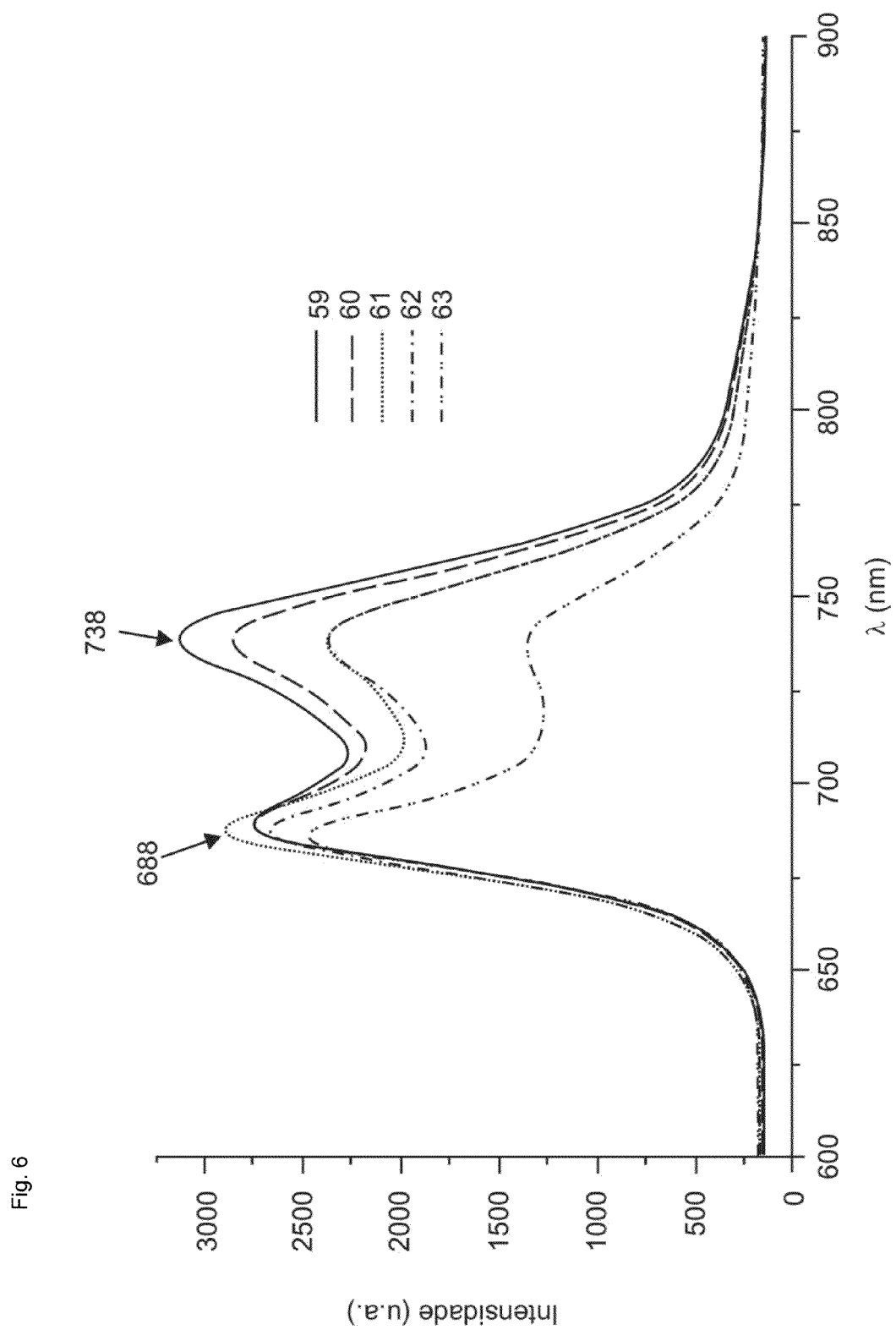
FIG. 6—Typical emission spectra of leaves of Hamlin orange with rootstocks of "Cravo" lime obtained in the portable system of laser induced fluorescence spectroscopy (LIFS) developed and built at LOLEIA.

In the graph of FIG. 6, a typical spectra obtained in the portable system with laser at 561 nm for Hamlin in "Cravo" lime rootstocks are presented. This set of samples presents healthy plants (59), with Decline (60), with Citrus Sudden Death (61), with asymptomatic Greening (62) and symptomatic Greening (63).

Figure 7:
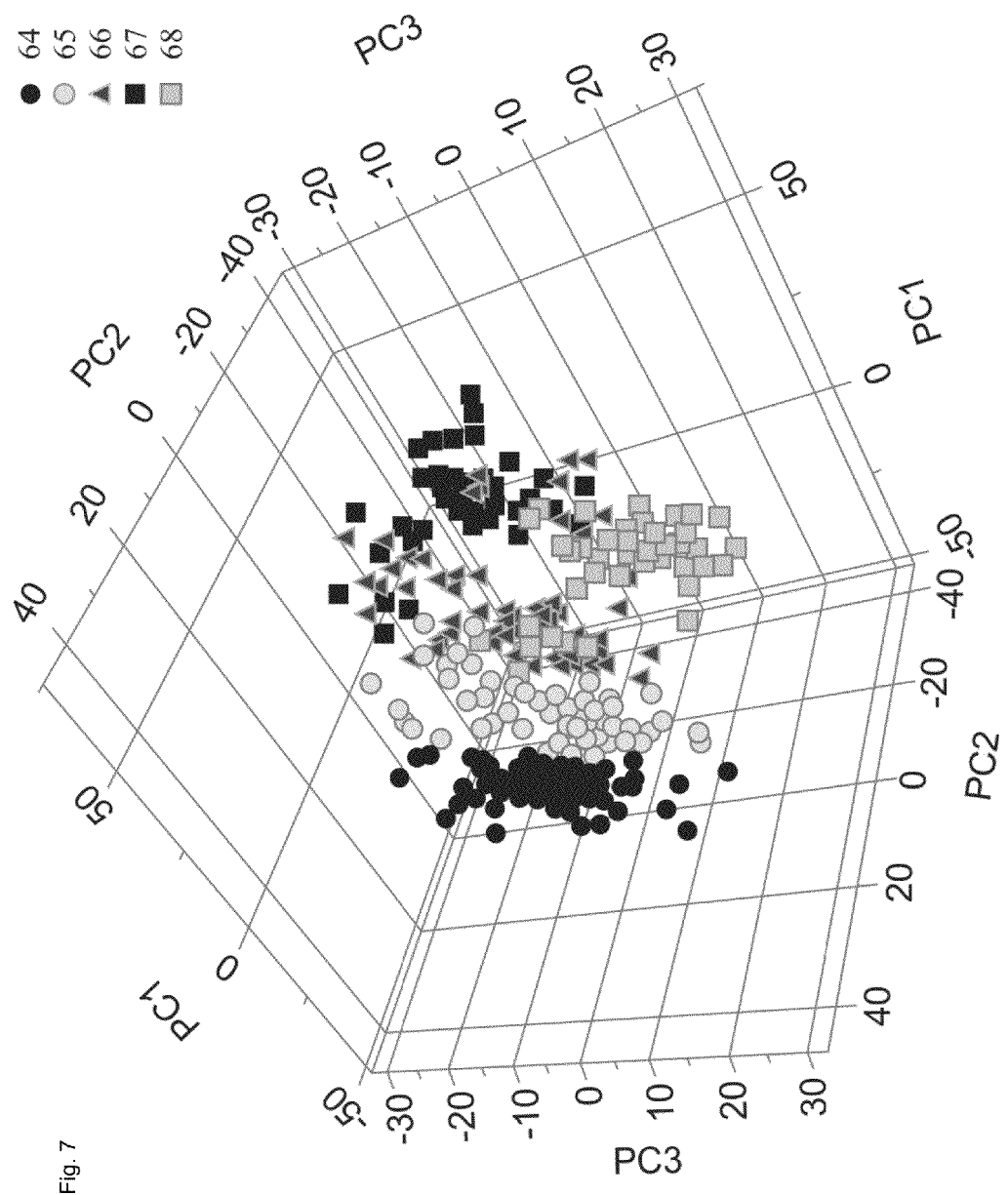
FIG. 7—PCA graphs generated through the spectra of leaves of the Hamlin orange tree with rootstocks of healthy "Cravo" lime and sick ones with AG, SG, CSD and Decline in the rainy season. All the spectra were obtained in the portable system of laser induced fluorescence spectroscopy (LIFS) developed and built at LOLEIA.

PCA analyses were performed with the data of the whole set of collected leaves for a better separation of diseases, as shown in FIG. 7, containing the same type of samples: healthy (64), with CSD (65), with Decline (66), with asymptomatic Greening (67) and with symptomatic Greening (68).

From this set of data, a software was constructed which classifying model is capable of performing the diagnosis of Hamlin leaves in "Cravo" lime rootstocks with a precision above 80%.

That which is claimed:

1. A method for diagnosis of diseases and stresses in higher plants of an orchard, consisting of the following steps:
   a) Constructing a database of spectra, by collecting the emission spectrum of at least 150 leaves from sick trees and 150 leaves from healthy trees;
   Calibrating a classifying software and developing a classifying model, based on the database of spectra and using tools of machine learning, statistics and/or mathematics;
   b) Collecting at least 03 leaves from georeferenced trees of the orchard to be analyzed;
   c) Detecting and measuring the fluorescence emission spectrum of all the leaves collected in (b) to generate spectra;
   d) Analyzing the spectra generated in (c) using the classifying software and providing a diagnosis result;
   e) Generating a report for each tree based on prevalence of resulting diagnosis obtained from analyzed spectra of the collected leaves; and
   f) Based on georeference identification of each georeferenced tree and on the report for each tree, constructing a health status map of the orchard.

2. The method for diagnosis of diseases and stresses in higher plants according claim 1, wherein the method is for the diagnosis of Greening disease in citrus.

3. The method according to claim 2, wherein the method is for the diagnosis of Greening disease in citrus with different combinations of canopy and rootstocks.

4. The method according to claim 1, wherein the method is used for the elaboration of a health map of the orchard.

5. The method for the diagnosis of diseases and stresses in higher plants according to claim 1, wherein the signal is diffracted and detected by a mini spectrometer.

6. The method for the diagnosis of diseases and stresses in higher plants according to claim 1, wherein the calibration of the classifying software is performed using tools of machine learning.

7. The method for the diagnosis of diseases and stresses in higher plants according to claim 1, wherein the method uses a dedicated classifying software.

8. The method for the diagnosis of diseases and stresses in higher plants according to claim 1, wherein the variations in the fluorescence spectra reflect the result of alterations in the chemical composition of the constituents of the plants.

9. The method for the diagnosis of diseases and stresses in higher plants according to claim 8, wherein the constituents are fluorescent.

10. The method according to claim 9, wherein the fluorescent constituents are photosynthetic pigments of the plant.

11. The method according to claim 9, wherein the fluorescent constituents are, mainly, chlorophyll a and b, and some accessory pigments, such as carotenoids and xanthophylls.

12. The method for the diagnosis of diseases and stresses in higher plants according to claim 1, wherein the leaves fluoresce under wavelength between 600 and 800 nm.

13. The method for the diagnosis of diseases and stresses in higher plants according to claim 1, wherein the wavelength used for the diagnosis of the Greening diseases is around 561 nm.

14. A system wherein the method according to claim 1 is used in association with an apparatus for the diagnosis of diseases and stresses in higher plants of an orchard, the system comprising an excitation source, an optical cable of excitation, an adjustable optical filter, an optical fiber adaptor, a mixed optical cable, a probe, an emission optical cable, a mini spectrometer and a data processing classifying software, for the diagnosis of diseases and stresses in higher plants, through the spectroscopy of fluorescence emission, wherein:
   a. the excitation light provided by the excitation source is conducted to the leaf through the optical cable of excitation connected to the probe;
   b. the signal diffracted is captured by the probe and conducted by the emission optical cable connected to the mini spectrometer to generate spectra; and
   c. the mini spectrometer communicates the spectra by means of a computer to the data processing classifying software, the data processing classifying software to provide the diagnosis result by using a classifying model, which is developed based on a database of spectra constructed by prevalence of resulting diagnosis that collecting the emission spectrum of at least 150 leaves from sick trees and 150 leaves from healthy trees and applying tools of machine learning, statistics and/or mathematics.

15. An apparatus for the diagnosis of diseases and stresses in higher plants of an orchard, the apparatus comprising an excitation source, an optical cable of excitation, an adjustable optical filter, an optical fiber adaptor, a mixed optical cable, a probe, an emission optical cable, a mini spectrometer and a data processing classifying software, wherein:
   a. the excitation light provided by the excitation source is conducted to the leaf through the optical cable of excitation connected to the probe;
   b. the signal diffracted is captured by the probe and conducted by the emission optical cable connected to the mini spectrometer to generate spectra; and
   c. the mini spectrometer is configured to communicate the spectra by means of a computer to the data processing classifying software,
   the data processing classifying software to provide a diagnosis result by using a classifying model, which is developed based on a database of spectra constructed by prevalence of resulting diagnosis that collecting the emission spectrum of at least 150 leaves from sick trees and 150 leaves from healthy trees and applying tools of machine learning, statistics and/or mathematics.

16. The apparatus for the diagnosis of diseases and stresses in higher plants according to claim 15, wherein the excitation source of fluorescence is bulb, LED or laser.

17. The apparatus according to claim 15, wherein the excitation source of fluorescence emits radiation in the UV range up to visible (200 to 700 nm).

18. The apparatus according to claim 15, wherein the excitation light is conducted to the leaf through optical fiber.

19. The apparatus according to claim 15, wherein the signal capturing is performed through optical fiber.

20. The apparatus according to claim 15, wherein the signal is diffracted by diffraction grating.

21. The apparatus according to claim 15, wherein the diagnosis and analysis software uses machine learning, statistical and/or mathematical models.

22. The apparatus according to claim 15, wherein the apparatus is responsible for performing the spectrometric measurements of fluorescence emission.

23. The apparatus according to claim 15, wherein the mixed optical cable comprises excitation optical fibers and optical fibers to capture the emission.

24. The apparatus according to claim 22, wherein the mixed optical cable comprises 6 excitation optical fibers and 1 optical fiber to capture the emission.

25. The apparatus according to claim 15, wherein the detection of the signal occurs through the array of calibrated photodiodes.

\* \* \* \* \*